US010078885B2

United States Patent
Aguirre-Valencia et al.

(10) Patent No.: US 10,078,885 B2
(45) Date of Patent: *Sep. 18, 2018

(54) IMAGE ANNOTATION USING A HAPTIC PLANE

(71) Applicant: EchoPixel, Inc., Los Altos Hills, CA (US)

(72) Inventors: Sergio Aguirre-Valencia, Santa Clara, CA (US); William Johnsen, Sunnyvale, CA (US); Anthony Chen, Berkeley, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/199,701

(22) Filed: Jun. 30, 2016

(65) Prior Publication Data

US 2016/0314558 A1    Oct. 27, 2016

Related U.S. Application Data

(63) Continuation of application No. 14/120,519, filed on May 28, 2014, now Pat. No. 9,384,528.

(51) Int. Cl.
*G06T 15/00* (2011.01)
*G06T 3/20* (2006.01)
(Continued)

(52) U.S. Cl.
CPC ............... *G06T 3/20* (2013.01); *G06F 3/016* (2013.01); *G06F 17/241* (2013.01);
(Continued)

(58) Field of Classification Search
CPC ... G06T 3/20; G06T 3/60; G06T 2207/30004; G06T 2210/41; G06T 19/20;
(Continued)

(56) References Cited

U.S. PATENT DOCUMENTS

| | | | |
|---|---|---|---|
| 5,548,694 A * | 8/1996 | Frisken Gibson | G06T 15/10 345/424 |
| 7,236,618 B1 * | 6/2007 | Chui | G06F 3/016 382/128 |

(Continued)

FOREIGN PATENT DOCUMENTS

| | | | |
|---|---|---|---|
| EP | 2538685 | 12/2012 | H04N 13/00 |
| WO | WO 2013/018004 | 2/2013 | H04N 13/04 |

OTHER PUBLICATIONS

Frank Lindseth et al., "Multimodal Image Fusion in Ultrasound-Based Neruonavigation: Improving Overview and Interpretation by Integrating Preoperative MRI with Intraoperative 3D Ultrasound", Computer Aided Surgery vol. 8, No. 2, pp. 49-69, Jan. 1, 2003.

(Continued)

*Primary Examiner* — Phu K Nguyen
(74) *Attorney, Agent, or Firm* — Steven Stupp (57) ABSTRACT

During an analysis technique, a three-dimensional (3D) image of a portion of an individual is transformed to facilitate accurate determination of detailed annotation of an anatomical structure (such as: specifying the size of the anatomical structure based on annotation markers, an orientation of the anatomical structure, a direction of the anatomical structure and/or a location of the anatomical structure). In particular, in response to receiving information specifying a two-dimensional (2D) plane having an angular position in the 3D image, the 3D image is translated and rotated from an initial position and orientation so that the 2D plane is presented in an orientation parallel to a reference 2D plane of a display. Then, after information specifying the detailed annotation in the 2D plane is received, the 3D image is translated and rotated back to the initial position and orientation.

20 Claims, 7 Drawing Sheets

(51) Int. Cl.
- *G06T 3/60* (2006.01)
- *G06F 3/01* (2006.01)
- *G06T 19/00* (2011.01)
- *G06F 17/24* (2006.01)
- *G06F 19/00* (2018.01)
- *G06T 19/20* (2011.01)

(52) U.S. Cl.
CPC .............. *G06F 19/321* (2013.01); *G06T 3/60* (2013.01); *G06T 19/00* (2013.01); *G06T 19/20* (2013.01); *G06T 2207/30004* (2013.01); *G06T 2210/41* (2013.01); *G06T 2219/004* (2013.01)

(58) Field of Classification Search
CPC ... G06T 2219/004; G06T 19/00; G06F 3/016; G06F 17/241; G06F 19/321
USPC .......................................... 345/419, 424, 632
See application file for complete search history.

(56) References Cited

U.S. PATENT DOCUMENTS

| | | | | |
|---|---|---|---|---|
| 8,654,150 B2* | 2/2014 | Haskell | ................... | G06T 17/00 345/632 |
| 8,754,888 B2* | 6/2014 | Virtue | ................... | G06T 7/174 345/424 |
| 8,819,591 B2* | 8/2014 | Wang | ................... | G06F 19/3437 715/850 |
| 8,968,320 B2* | 3/2015 | Park | ................... | A61B 5/055 606/88 |
| 9,011,456 B2* | 4/2015 | Ranawat | ................... | A61F 2/4609 606/91 |
| 9,384,528 B2* | 7/2016 | Aguirre-Valencia | ..... | G06T 3/20 |
| 9,830,700 B2* | 11/2017 | Yee | ................... | G06T 7/0012 |
| 2006/0020204 A1 | 1/2006 | Serra et al. | ................... | 600/437 |

OTHER PUBLICATIONS

T. A. Nagelhus Hernes, "Stereoscopic Navigation-Controlled Dispaly of Preoperative MRI with Intraoperative 3D Ultrasound in Planning and Guidance of Neurosurgery: New Technology for Minimally Invasive Image-Guided Surgery Approaches", Minimally Invasive Neurosurgery vol. 46, No. 3, pp. 129-137, Jun. 1, 2003.

Extended European Search Report for European Patent Application Serial No. 17164018.8, dated Nov. 10, 2017.

Response to Extended European Search Report for European Patent Application Serial No. 17164018.8, dated May 25, 2018.

* cited by examiner

IMAGE ANNOTATION USING A HAPTIC PLANE

CROSS REFERENCE TO RELATED APPLICATION

This application claims priority under 35 U.S.C. 120 as a Continuation Patent Application of U.S. patent application Ser. No. 14/120,519, "Image Annotation Using a Haptic Plane," filed on May 28, 2014, the contents of which are herein incorporated by reference.

BACKGROUND

Field

The present disclosure generally relates to computer-based techniques for annotating a feature in an image. More specifically, the present disclosure relates to a computer-based technique for translating and rotating a user-specified two-dimensional plane in a three-dimensional image so that detailed annotation of an anatomical structure can be accurately determined.

Related Art

Medical imaging is a widely used approach in medicine for acquiring images of the human body. For example, medical imaging of a patient may involve one or more modalities such as: computed tomography, ultrasound, magnetic resonance imaging, and x-ray imaging. The resulting images are typically evaluated by a physician (such as a radiologist) to diagnose disease and to guide subsequent treatment (e.g., surgical procedures).

However, it can be difficult to interpret medical images. In particular, it is often difficult to distinguish abnormal features from normal anatomical features. Moreover, many of the abnormal features identified during evaluation of medical images are artifacts (or so-called 'false positives') that do not affect the health of the patient.

In addition, it can be challenging to compare medical images that are acquired from different perspectives or in which the patient has a different orientation relative to an imaging apparatus (to identify abnormal features). For example, many of the organs in the human body are non-rigid and have mechanical degrees of freedom (such as rotation, compression and extension) that allow these organs to change their position and shape in the different orientations. These problems can degrade the accuracy of the evaluations of medical images, resulting in false positives, false negatives (where abnormal features are not identified), unnecessary medical procedures and adverse patient outcomes. Hence, there is a need for an improved analysis technique for evaluating medical images.

SUMMARY

The disclosed embodiments relate to a computer system that facilitates detailed annotation of an anatomical structure. During operation, the computer system provides, on a display, a three-dimensional (3D) image of a portion of an individual, where the 3D image has an initial position and orientation. Then, the computer system receives information specifying a two-dimensional (2D) plane in the 3D image, where the 2D plane has an angular position relative to the initial orientation. Moreover, the computer system translates and rotates the 3D image so that the 2D plane is presented on a reference 2D plane of the display with an orientation parallel to the reference 2D plane (so that the normal to the 2D plane is parallel to the normal of the reference 2D plane).

Next, the computer system receives information specifying the detailed annotation in the 2D plane, where the detailed annotation includes: a size of the anatomical structure based on annotation markers, an orientation of the anatomical structure, a direction of the anatomical structure and/or a location of the anatomical structure. After the annotation is complete, the computer system translates and rotates the 3D image back to the initial position and orientation.

Note that the 3D image may include a stereoscopic image. In some embodiments, the 3D image corresponds to one of: a cross section of a volume, and a multiplanar-reconstruction image.

Moreover, the information specifying the detailed annotation may be received from an interaction tool. Alternatively or additionally, the information specifying the detailed annotation may correspond to haptic interaction between a digit of a user and the display.

In some embodiments, prior to translating and rotating the 3D image back to the initial orientation, the computer system receives a command indicating that the annotation is complete.

Furthermore, the 2D plane may be positioned at a zero parallax position so that 3D information in the 2D plane is perceived as 2D information.

Additionally, the angular position may be at an oblique angle relative to a symmetry axis of the individual.

Another embodiment provides a method that includes at least some of the operations performed by the computer system.

Another embodiment provides a computer-program product for use with the computer system. This computer-program product includes instructions for at least some of the operations performed by the computer system.

BRIEF DESCRIPTION OF THE FIGURES

Note that like reference numerals refer to corresponding parts throughout the drawings. Moreover, multiple instances of the same part are designated by a common prefix separated from an instance number by a dash.

DETAILED DESCRIPTION

Embodiments of a computer system, a technique for facilitating detailed annotation of an anatomical structure, and a computer-program product (e.g., software) for use with the computer system are described. During this analysis technique, a three-dimensional (3D) image of a portion of an individual is transformed to facilitate accurate determination of detailed annotation of the anatomical structure. In particular, in response to receiving information specifying a two-dimensional (2D) plane having an angular position in the 3D image, the 3D image is translated and rotated from an initial position and orientation so that the 2D plane is presented in an orientation parallel to a reference 2D plane of a display. Then, after information specifying the detailed annotation in the 2D plane is received, the 3D image is translated and rotated back to the initial position and orientation. Note that the detailed annotation may include: specifying the size of the anatomical structure based on annotation markers, an orientation of the anatomical structure, a direction of the anatomical structure and/or a location of the anatomical structure.

By facilitating accurate determination of the annotation markers, the analysis technique may improve the accuracy of evaluations or interpretations of medical images by healthcare professionals (such as radiologists). In the process, the analysis technique may reduce patient anxiety associated and may reduce the cost (including unnecessary medical procedures and/or diagnostic testing) and adverse patient outcomes (including mortality) associated with incorrect determination of the sizes of anatomical structures.

In the discussion that follows, the medical images are of an individual. More generally, the medical images may be of an animal that is living or deceased. Furthermore, the medical images of the object may be acquired using a wide variety of medical-imaging modalities, including: a computed-tomography or CT scan, histology, an ultrasound image, a magnetic resonance imaging or MRI scan, x-ray imaging, or another type of two-dimensional (2D) image slice depicting volumetric information. As an illustrative example, the object is the colon, and the medical images are acquired using CT scans (e.g., a CT colonography or CT virtual colonoscopy). However, the images may be a variety of organs and aspects of anatomy, as well as a variety of procedures (such as mammography or lung-cancer screening). In general, the object may be a non-rigid object that includes medical degrees of freedom, such as: rotation, compression and extension. Thus, the object may include organs and anatomical features or structures such as: a portion of a small intestine, a portion of a large intestine, a portion of a non-rigid organ, a portion of the vascular system (such as the heart, an artery or a vein), and/or a portion of an organ that includes a cavity with a fluid or a liquid.

Furthermore, in the discussion that follows, annotation markers are used as an illustration of detailed annotation of the anatomical structure. However, more generally, 'detailed annotation' should be understood to include: specifying the size of the anatomical structure based on annotation markers, an orientation of the anatomical structure, a direction of the anatomical structure and/or a location of the anatomical structure. This detailed annotation may facilitate tracing and/or measurement of the anatomical structure.

Figure 1:
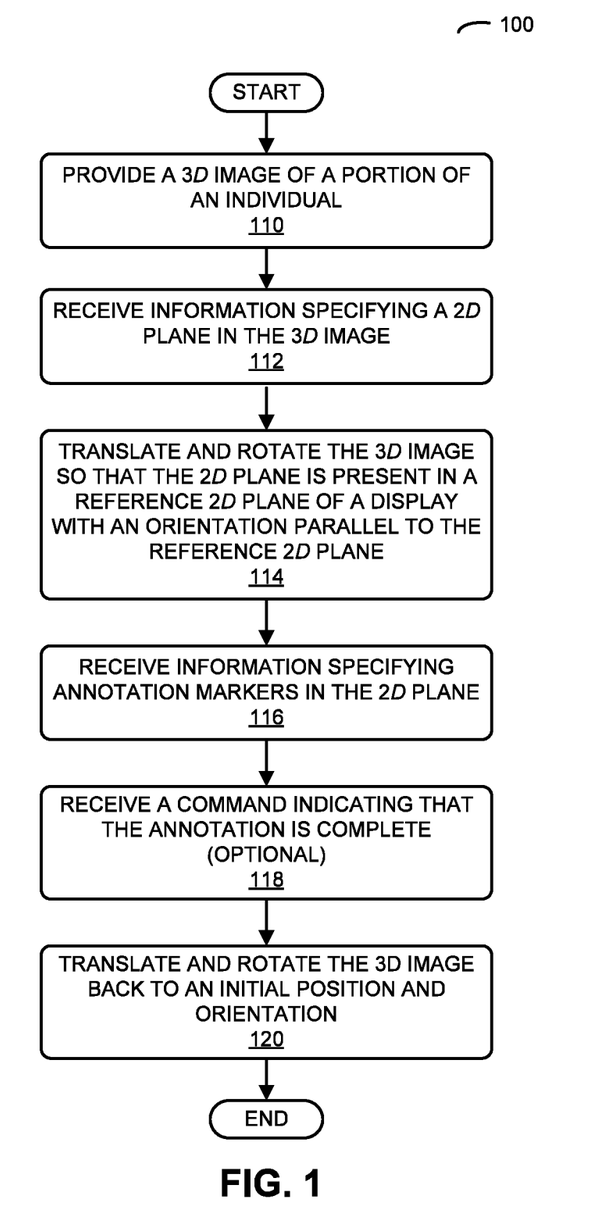
FIG. 1 is a flow chart illustrating a method for measuring a size of an anatomical structure in accordance with an embodiment of the present disclosure.

We now describe embodiments of the analysis technique. FIG. 1 presents a flow chart illustrating a method 100 for measuring the size of an anatomical structure, which may be performed by a computer system (such as computer system 600 in FIG. 6). During operation, the computer system provides, on a display, a 3D image of a portion of an individual (operation 110), where the 3D image has an initial position and orientation. Note that the 3D image may include a stereoscopic image. In an exemplary embodiment, the 3D image includes representations of human anatomy, such as input data that is compatible with a Digital Imaging and Communications in Medicine (DICOM) standard. In some embodiments, the 3D image corresponds to a cross section of the volume and/or a multiplanar-reconstruction image.

Then, the computer system receives (or accesses in a computer-readable memory) information specifying a 2D plane in the 3D image (operation 112), where the 2D plane has an angular position relative to the initial orientation. The angular position may be at an oblique or arbitrary angle relative to a symmetry axis of the individual (such as a symmetry axis in the axial, coronal and/or sagittal planes).

Moreover, the computer system translates and rotates the 3D image so that the 2D plane is presented on a reference 2D plane of the display with an orientation parallel to the reference 2D plane (operation 114). This 2D plane may be positioned at a zero parallax position so that 3D information in the 2D plane is perceived as 2D information.

Next, the computer system receives information specifying annotation markers in the 2D plane (operation 116), where the annotation markers specify the size of the anatomical structure. For example, the information specifying the annotation markers may be received from an interaction tool (such as by tracking the location or position of the interaction tool relative to the display). Alternatively or additionally, the information specifying the annotation markers may correspond to haptic interaction between a digit of a user and the display. Note that the parallel orientation and/or zero parallax may facilitate accurate determination of annotation markers by a user of the computer system, who may specify the annotation markers.

In an exemplary embodiment, the anatomical structure includes: a portion of a small intestine, a portion of a large intestine (such as a polyp candidate), a portion of an organ, a portion of the vascular system (such as an artery or a vein), a portion of an organ that includes a cavity with a fluid (such as a valve in the heart), a portion of a tumor, etc. Thus, the anatomical structure may include normal and/or abnormal anatomical structures.

After the annotation is complete, the computer system translates and rotates the 3D image back to the initial position and orientation (operation 120). For example, the user may indicate when the annotation is complete. Therefore, in some embodiments, prior to translating and rotating the 3D image back to the initial orientation (operation 120), the computer system optionally receives a command indicating that the annotation is complete (operation 118).

Figure 2:
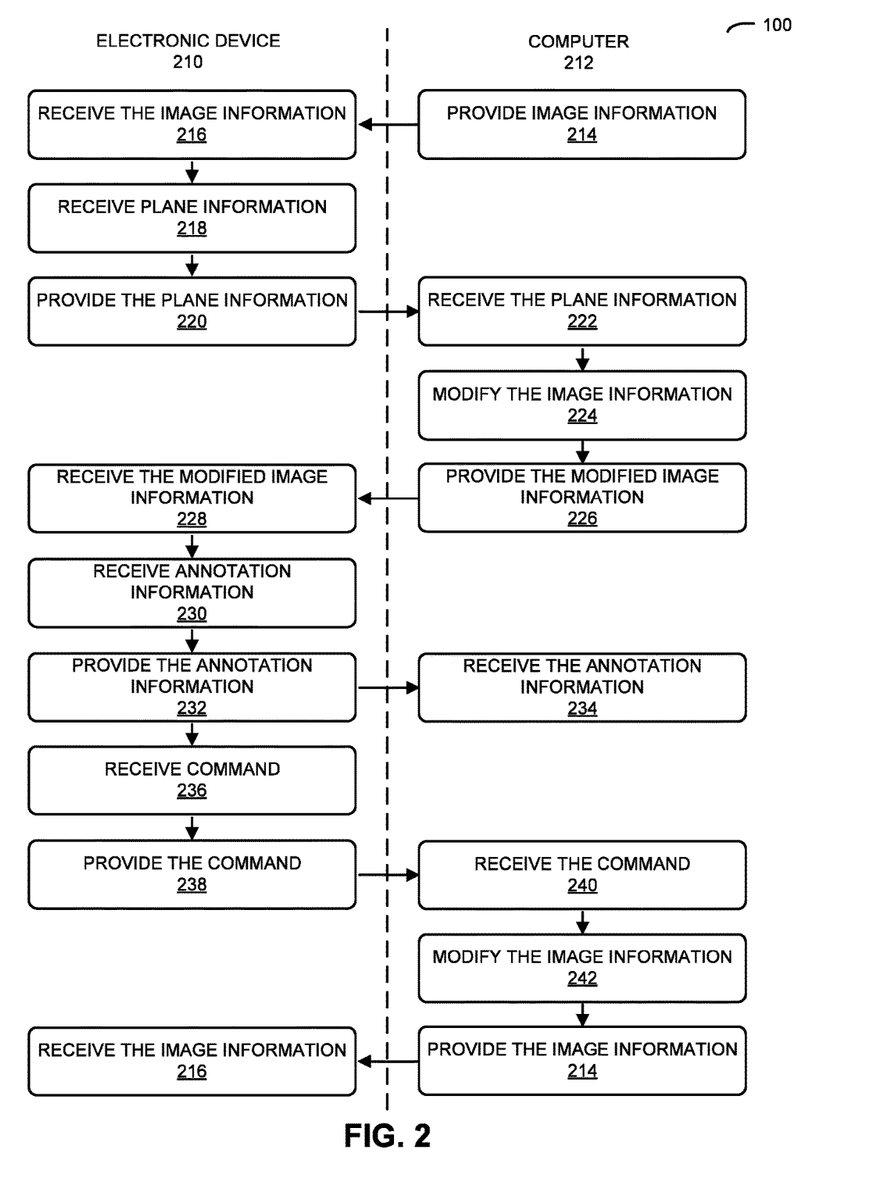
FIG. 2 is a flow chart illustrating the method of FIG. 1 in accordance with an embodiment of the present disclosure.

In an exemplary embodiment, the analysis technique is implemented using one or more electronic devices (such as a computer or a portable electronic device, e.g., a cellular telephone) and one or more computers (such as a server or a computer system), which communicate through a network, such as a cellular-telephone network and/or the Internet. This is illustrated in FIG. 2, which presents a flow chart illustrating method 100 (FIG. 1).

During the method, computer 212 may provide (operation 214) image information specifying the 3D image of the portion of the individual. Electronic device 210 (which may include a display) may receive the image information (operation 216) and may present the 3D image to a user (e.g., on the display).

Figure 6:
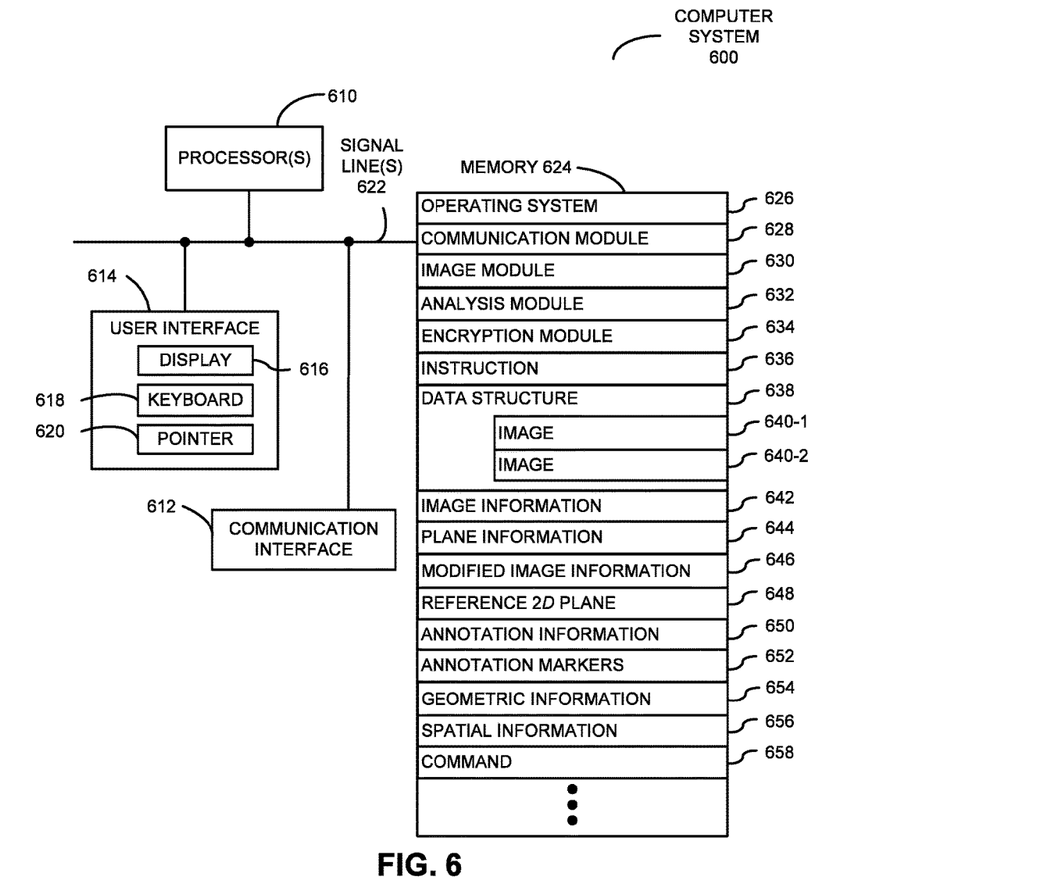
FIG. 6 is a block diagram illustrating a computer system that performs the method of FIGS. 1 and 2 in accordance with an embodiment of the present disclosure.
Figure 7:
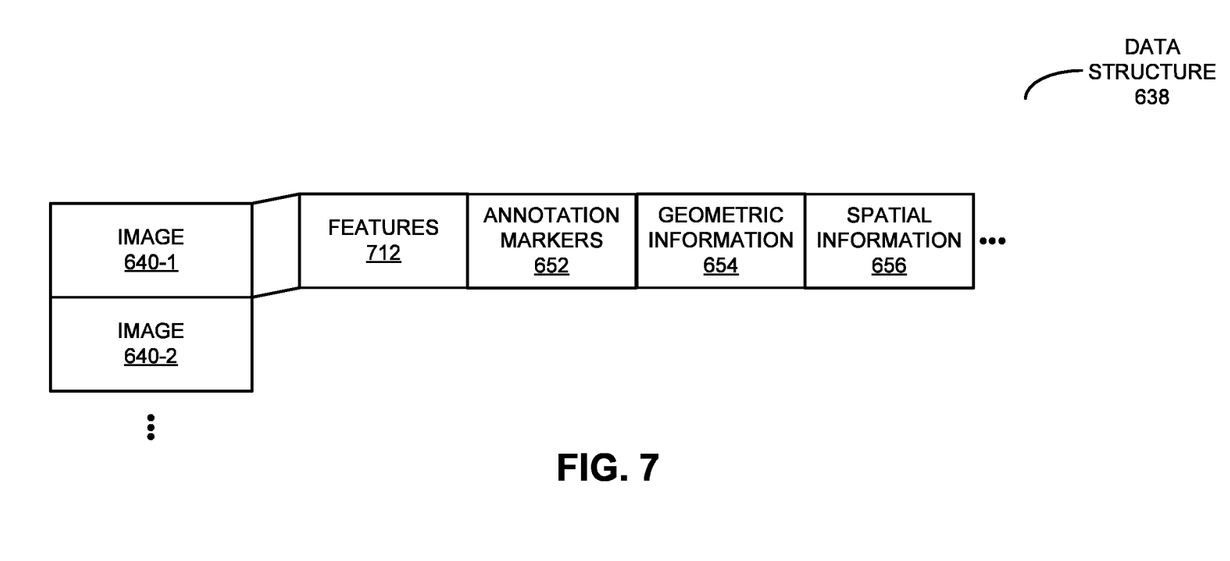
FIG. 7 is a block diagram illustrating a data structure that includes image data in accordance with an embodiment of the present disclosure.

Then, electronic device 210 may receive plane information (operation 218) specifying the 2D plane in the 3D image. For example, while interacting with the displayed 3D image using an interaction tool (such as a stylus) and/or by touching the display (in embodiments where the display is touch sensitive), the user (such as a physician or a radiologist) may provide the plane information. Moreover, electronic device 210 may provide (operation 220) and computer 212 may receive the plane information (operation 222). Alternatively, in some embodiments the plane information was previously provided or was predefined. In these embodiments, computer 212 may access the plane information in a computer-readable memory. In some embodiments, computer 212 determines the 2D plane based on previous user actions, metadata associated with the 3D image (such as metadata that indicates a reason for a medical-imaging study, e.g., a probable or suspected diagnosis) and/or computer-assisted detection (which may identify the anatomical structure and, thus, the 2D plane).

Next, computer 212 may modify the image information (operation 224) to translate and rotate the 3D image so that the 2D plane is presented in the reference 2D plane of the display with the orientation parallel to the reference 2D plane. This modification may involve computer 212 accessing data specifying one or more images in a computer-readable memory (such as data structure 638 in FIGS. 6 and 7). Moreover, computer 212 may provide (operation 226) and electronic device 210 may receive the modified image information (operation 228), which may then be presented to the user (e.g., on the display).

Furthermore, electronic device 210 may receive annotation information (operation 230) specifying the annotation markers in the 2D plane. For example, while interacting with the displayed image using the interaction tool and/or by touching the display, the user may provide the annotation information. Electronic device 210 may provide (operation 232) and computer 212 may receive (operation 234) the annotation information.

Additionally, electronic device 210 may receive the command (operation 236) indicating that the annotation is complete. In response, electronic device 210 may provide (operation 238) and computer 212 may receive the command (operation 240). Then, computer 212 may modify the image information (operation 242) to translate and rotate the 3D image back to the initial position and orientation, and computer 212 may repeat operation 214 and electronic device 210 may repeat operation 216.

In some embodiments of method 100 (FIGS. 1 and 2), there are additional or fewer operations. Moreover, the order of the operations may be changed, and/or two or more operations may be combined into a single operation.

In an exemplary embodiment, the analysis technique may allow the size of the anatomical structure to be accurately determined and specified by a user of the computer system while viewing the 3D image. The 3D image may include so-called True 3D, which combines stereoscopic images (via image parallax) with motion parallax and prehension associated with interaction of the user with the stereoscopic images using the interaction tool and/or one or more of the user's fingers. True 3D may provide a better understanding of anatomical shapes and structures because it integrates all three dimensions and corresponding depth cues in a single view.

However, if the translation and rotation of the 3D image in the analysis technique are not performed, the reader (such as the user of the computer system, e.g., a radiologist) may have the hard task of performing a mental rotation or an imagined perspective shift in order to determine or specify the annotation markers. Instead, by transforming the 3D image during a haptic-plane or annotation mode of operation, the analysis technique allows the reader to offload spatial cognition to their perceptual motor system (via the interaction tool and/or one or more of the user's fingers), which can reduce the intensity of 3D image interpretation and can significantly increase the accuracy of determined size of the anatomical structure. Consequently, the analysis technique may reduce perceptual errors when reading 3D images.

Figure 3:
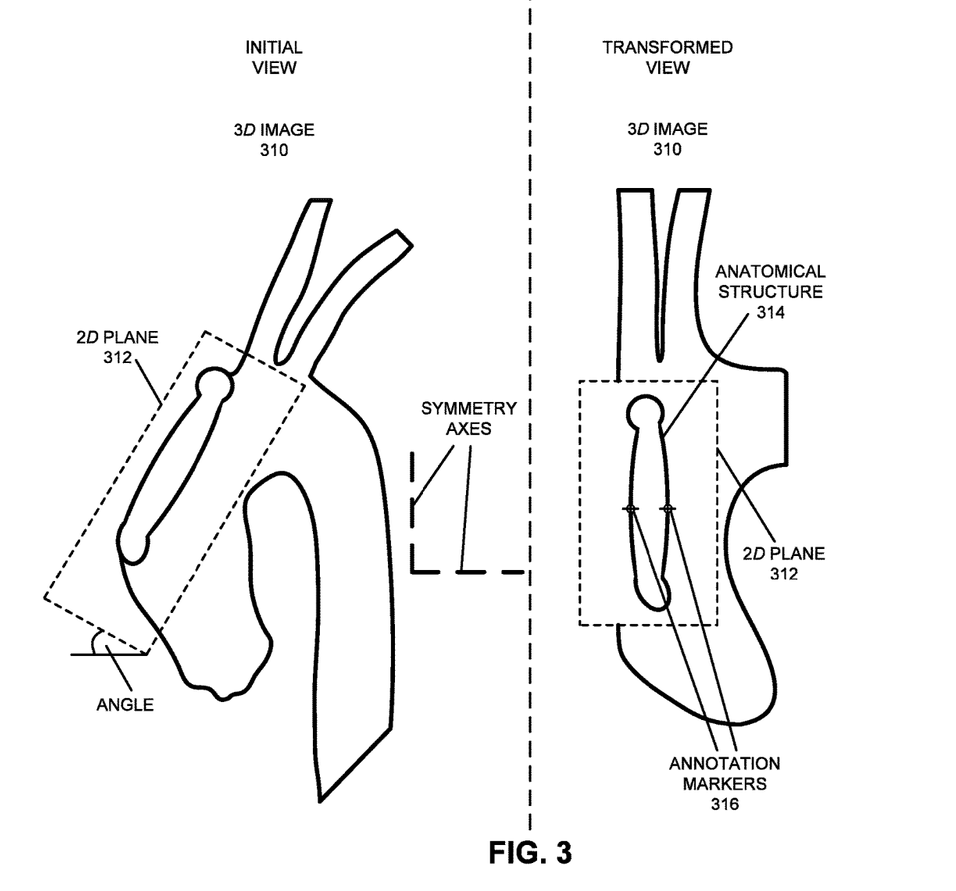
FIG. 3 is a drawing of illustrating transforming a medical image of an individual in accordance with an embodiment of the present disclosure.

The translation and rotation operations are shown in FIG. 3, which presents a drawing of illustrating transforming a medical image of an individual. In particular, 2D plane 312 in 3D image 310 is rotated and translated so that it is parallel to the plane of FIG. 3 (which represents the reference 2D plane of a display that displays 3D image 310). This parallel orientation facilitates determining or specifying of annotation markers 316 associated with anatomical structure 314.

We now describe an illustration of the calculations used in the analysis technique. The analysis technique may be used during a haptic-plane or annotation mode of operation. This annotation mode of operation may use three elements: the 2D plane (which is sometimes referred to as a 'clip plane' or a 'cut plane') that may be applied to an object (which, for purposes of illustration, can be volume or an image dataset used to create a 2D multiplanar-reconstruction-image slice or volume), the reference 2D plane (which is sometimes referred to as a 'physical plane') of the display, and the object. Note that the 2D plane may be defined as a point and a normal, where the point indicates the location of the 2D plane and the normal indicates the orientation of the 2D plane. Similarly, the reference 2D plane may be defined as a point and normal, where the point is the world center or origin (0, 0, 0) and the normal creates a −30° rotation about the x axis.

The purpose of the annotation technique may be to transform (which, in general, involves translation and/or rotation) an oblique cross section of a volume or an oblique 2D multiplanar-reconstruction image (created by the application of the 2D plane or a clip plane on the image data) to the reference 2D plane. Then, once on the reference 2D plane, the cross section or 2D multiplanar-reconstruction image may maintain an orientation equal to the orientation of the reference 2D plane. Moreover, because the cross section of the volume or the multiplanar-reconstruction image is on the reference 2D plane, the user can rest his/her hand and may annotate (mark, measure, delineate, etc.) a 3D representation of the data with high confidence. Furthermore, once the annotation is complete, the cross section of the volume or the oblique 2D multiplanar-reconstruction image may be transformed (which, in general, involves translation and/or rotation) back to the original position.

The transformation may involve the following operations: start up, haptic-location identification, 2D plane preprocessing, haptic-rotation calculation, haptic-translation calculation, and application of the haptic transformation (including the haptic rotation and/or the haptic translation) about the haptic location to the object. The result of these operations may be that the cross section of the object is visible on the reference 2D plane of the display.

In particular, during the start-up operation, the original matrices for both the 2D plane and the object may be saved. These matrices may contain the location, orientation and scale. Similarly, during the haptic-location-identification operation, the original location of the 2D plane (which is sometimes referred to as the 'haptic location') may be saved to be used as a point from which to apply the haptic rotation. Moreover, during the 2D-plane-preprocessing operation the 2D plane may be rotated in place so that it is pointing up (so-called 'world up'), thereby removing any additional rotation except for the −30° rotation that may be required for the physical display (i.e., to the reference 2D plane). Furthermore, during the haptic-rotation-calculation operation, the rotation of the 2D plane to the reference 2D plane may be calculated (in this example, this may be a −30° rotation about the x axis) and the resulting rotation matrix used for this transformation (which is sometimes referred to as 'haptic rotation') may be saved. Additionally, during the haptic-translation-calculation operation, the translation needed to move the 2D plane to the reference 2D plane may be determined. The delta vector in this operation (which is sometimes referred to as 'haptic translation') may be saved. Finally, during the haptic-transformation operation, the haptic rotation may be applied to the object about the haptic location (the original position of the 2D plane), and then the haptic translation may be applied to the object (i.e., it may be translated by the same amount as the 2D plane).

Figure 4:
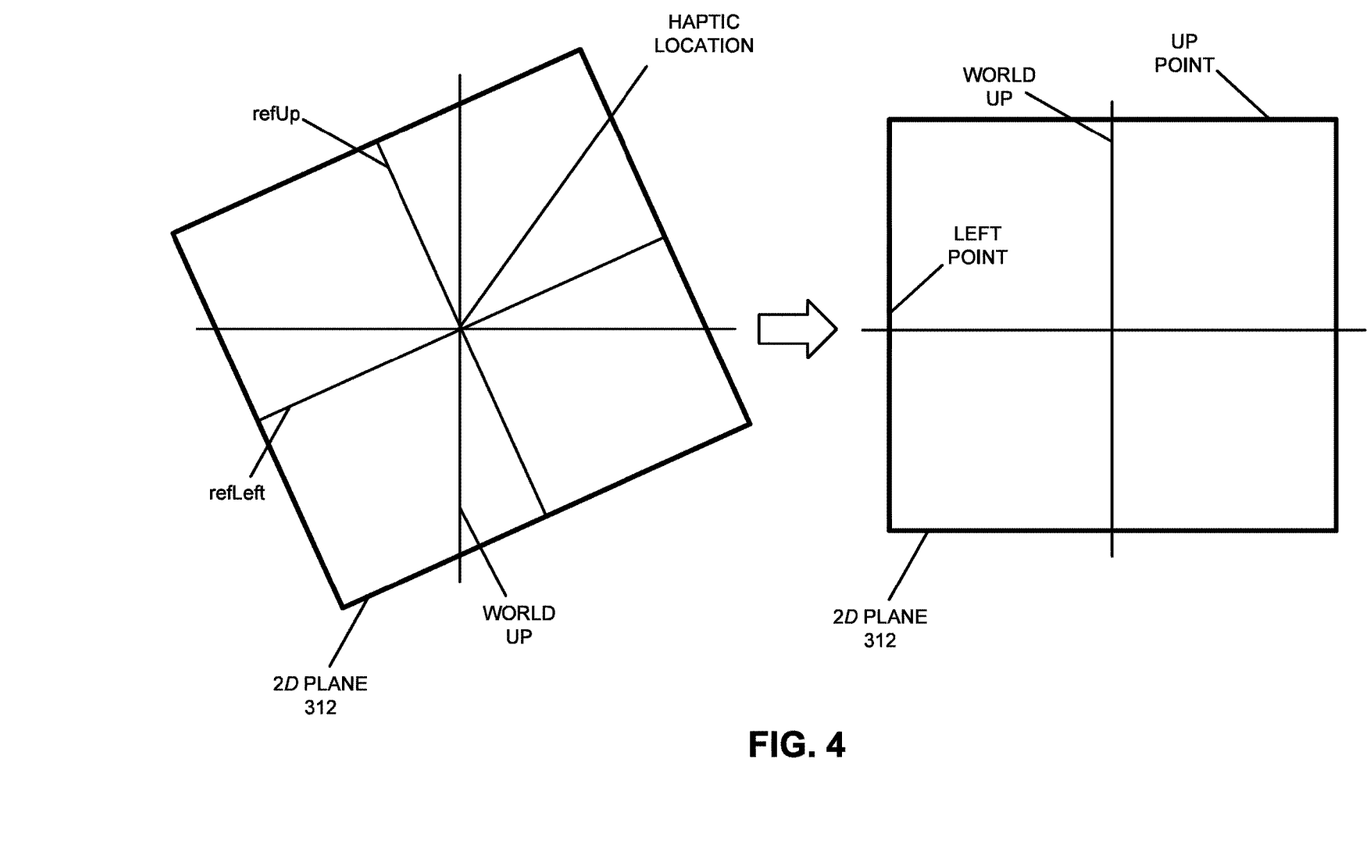
FIG. 4 is a drawing of illustrating transforming a medical image of an individual in accordance with an embodiment of the present disclosure.

We now describe embodiments of the 2D-plane preprocessing in more detail. The 2D-plane preprocessing is shown in FIG. 4, which presents a drawing of illustrating transforming a medical image of an individual. Note that, for clarity, only a portion of the medical image is shown. During the 2D-plane-preprocessing operation, a vector that has zero x component, but that still lies in the 2D plane, may be determined. This calculation may use two vectors refUp and refLeft, and may determine a third vector (the desiredVector) for which the determinant is zero (i.e., so that the three vectors lie on the 2D plane).

In particular, the current refUp and refLeft points may be identified. Then, the haptic point (location) may be identified. Moreover, the upVector may be calculated as refUp minus haptic point, and the leftVector may be calculated as refLeft minus haptic point. Next, the upVector and leftVector may be normalized. Furthermore, the z component of desiredVector may be calculated via evaluation of possibleVectors. The components of possibleVector1 may be:

$$possibleVector1[x] = 0,$$

$$possibleVector1[y] = \sqrt{1 - possibleVector1[z]^2}, \text{ and}$$

$$possibleVector1[z] = \frac{\left(leftVector_x \cdot upVector_z - upVector_z \cdot leftVector_z\right)}{\sqrt{\alpha \cdot \beta + \delta^2}}$$

where $\alpha = leftVector_x \cdot upVector_y - upVector_z \cdot leftVector_y$,
$\beta = leftVector_x \cdot upVector_y - upVector_x \cdot leftVector_y$, and
$\delta = leftVector_x \cdot upVector_z - upVector_x \cdot leftVector_z$.
Similarly, the components of possibleVector2 may be:

$$possibleVector2[x] = 0,$$

$$possibleVector2[y] = \sqrt{1 - possibleVector2[z]^2}, \text{ and}$$

$$possibleVector2[z] = \frac{-\left(leftVector_x \cdot upVector_z - upVector_z \cdot leftVector_z\right)}{\sqrt{\alpha \cdot \beta + \delta^2}}$$

where $\alpha = leftVector_x \cdot upVector_y - upVector_z \cdot leftVector_y$,
$\beta = leftVector_x \cdot upVector_y - upVector_x \cdot leftVector_y$, and
$\delta = leftVector_x \cdot upVector_z - upVector_x \cdot leftVector_z$.

Subsequently, the 3×3 determines of the possible vectors may be calculated as:

$$det1 = \begin{vmatrix} upVector_z & upVector_y & upVector_z \\ leftVector_x & leftVector_y & leftVector_z \\ possibleVector1[x] & possibleVector1[y] & possibleVector1[z] \end{vmatrix}$$

and $$det2 = \begin{vmatrix} upVector_z & upVector_y & upVector_z \\ leftVector_x & leftVector_y & leftVector_z \\ possibleVector2[x] & possibleVector2[y] & possibleVector2[z] \end{vmatrix}.$$

The desiredVector may be the possible vector with the smallest z component. In particular, if det1 is less than det2, the desiredVector may equal possibleVector1. Otherwise, if det2 is less than det1, the desiredVector may equal possibleVector2.

As described further below, the quaternion rotation from the upVector to the desiredVector may then be calculated, where $V_0$ equals the upVector and $V_1$ equals the desiredVector.

Note that the delta vector may be the difference between two quaternion rotations defined by two reference markers and a feature. In particular, a quaternion $\vec{q}$ may be an array containing a vector $\vec{v}$ and a scalar w. The scalar value may be the rotation angle θ in radians and the vector may be the unit vector about which the rotation takes place. Thus, $$\vec{q} = \langle \vec{v}, w \rangle$$

where w equals $q_3$ and $$\vec{v} = [q_0, q_1, q_2] = [x, y, z].$$

Moreover, a quaternion can represent a rotation by a rotation angle θ around a unit axis a. Note that if a has unit length, then $\vec{q}$ has unit length too. Thus, $$\vec{q} = \left[ a_x \sin\left(\frac{\theta}{2}\right), a_y \sin\left(\frac{\theta}{2}\right), a_z \sin\left(\frac{\theta}{2}\right), \cos\left(\frac{\theta}{2}\right) \right]$$

or $$\vec{q} = \left[ \vec{a} \sin\left(\frac{\theta}{2}\right), \cos\left(\frac{\theta}{2}\right) \right].$$

We now describe embodiments of the quaternion calculation in more detail. Given normalized vectors $V_0$ and $V_1$, $\vec{q}$ equals $$V_0 V_1^* = [V_0 \times V_1, V_0 \cdot V_1] = \left[ \hat{V} \sin\left(\frac{\theta}{2}\right), \cos\left(\frac{\theta}{2}\right) \right],$$

where $$\hat{V} = \frac{V_0 \times V_1}{\|V_0 \times V_1\|},$$

$$V_0 \cdot V_1 = \cos\left(\frac{\theta}{2}\right) = W,$$

and $$\vec{q}^* = [-V, W].$$

In an exemplary embodiment, 2·φ=upVector·desiredVector, qv=upVector⊗desiredVector (where ⊗ denotes a cross product), 2·φ=a cos(2·φ), and $$\phi = \frac{2 \cdot \varphi}{2}.$$

Then, the quaternion rotation scalar w may be $\cos(\phi)$ and the projection factor f for a unit vector of the quaternion may be $\sin(\phi)$. Consequently, the components of the quaternion may be:

$q[0]=w$, $q[1]=f \cdot qv[0]$, $q[2]=f \cdot qv[1]$, $q[3]=f \cdot qv[2]$,

Thus, the quaternion may be transformed into a 3×3 rotation matrix.

We now describe embodiments of the haptic-rotation calculation in more detail. First, the rotation to the reference 2D plane may be calculated. The result may be the current rotation matrix of the 2D plane, which may be stored as cutPlaneRotation. Then, cutPlaneRotation may be inverted. Using the desired end rotation (which may be a constant of −30° about the x axis), which in matrix notation may be represented as $$\begin{pmatrix} 1 & 0 & 0 \\ 0 & 0.5 & -\frac{\sqrt{3}}{2} \\ 0 & \frac{\sqrt{3}}{2} & 0.5 \end{pmatrix},$$

the 'delta' rotation (or deltaRotation) may be calculated by multiplying the end rotation by cutPlaneRotation.

We now describe embodiments of the haptic-translation calculation in more detail. Using the haptic location and the center of the physical display, the haptic translation may be calculated as: deltaVector[x] equal to physical display center[x]−haptic location[x], deltaVector[y] equal to physical display center[y]−haptic location[y], and deltaVector[z] equal to physical display center[z]−haptic location[z].

The results of the preceding calculations can be used to implement the haptic transformation. In particular, by using current 4×4 matrix of the object, a series of rotations and translations may be concatenated to place it at the reference 2D plane with the correct up rotation. For example, the haptic transformation for the object may be created by: translating the current matrix of the object by −1·haptic location. Then, the resulting matrix may be rotated by the haptic rotation, and may be translated by the haptic location. Finally, the resulting matrix may be translated by the haptic translation. Application of this matrix may result in the cross section of the object being visible in the 2D plane, and the 2D plane being moved to the reference 2D plane of the display.

While a particular set of calculations and operations are described in the preceding examples, in other embodiments there may be different calculations and operations (such as a different decomposition of the 2D plane preprocessing and the haptic-rotation calculation).

Figure 5:
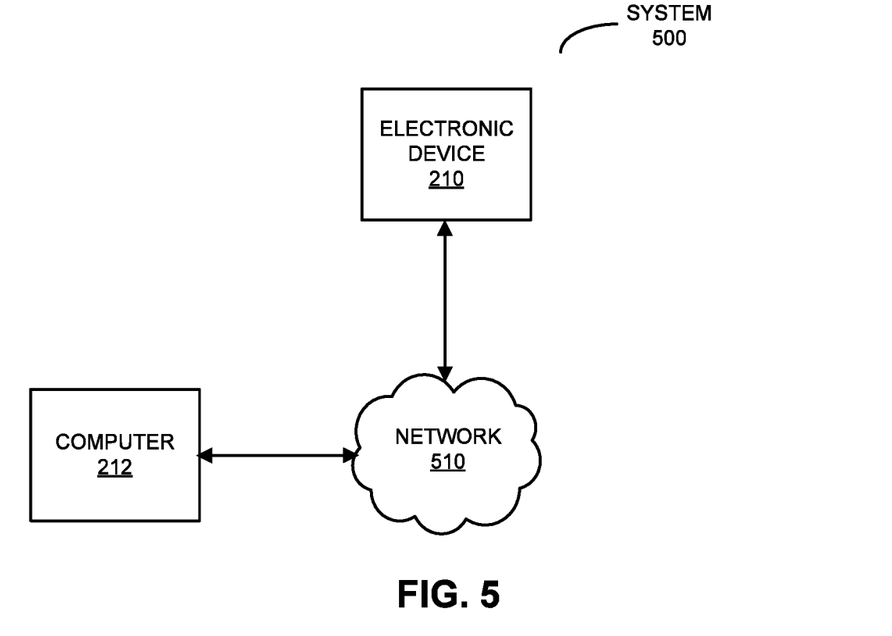
FIG. 5 is a block diagram illustrating a system that performs the method of FIGS. 1 and 2 in accordance with an embodiment of the present disclosure.

We now describe embodiments of a system and the computer system, and their use. FIG. 5 presents a block diagram illustrating a system 500 that can be used, in part, to perform operations in method 100 (FIGS. 1 and 2). In this system, during the analysis technique electronic device 210 may use a software product, such as a software application that is resident on and that executes on electronic device 210. (Alternatively, the user may interact with a web page that is provided by computer 212 via network 510, and which is rendered by a web browser on electronic device 210. For example, at least a portion of the software application may be an application tool that is embedded in the web page, and which executes in a virtual environment of the web browser. Thus, the application tool may be provided to electronic device 210 via a client-server architecture.) This software application may be a standalone application or a portion of another application that is resident on and which executes on electronic device 210 (such as a software application that is provided by computer 212 or that is installed and which executes on electronic device 210). In an exemplary embodiment, the software product may be medical-imaging software, such as software used by radiologists.

During the analysis technique, computer 212 may provide, via network 510, the image information specifying the 3D image of the portion of the individual. This image information may be received by electronic device 210 and may be presented to a user of electronic device 210 on a display as the 3D image.

Then, the user may provide the plane information specifying the 2D plane in the 3D image to electronic device 210, which may communicate, via network 510, the plane information to computer 212.

Next, computer 212 may modify the image information to translate and rotate the 3D image so that the 2D plane is presented in the reference 2D plane of the display with the orientation parallel to the reference 2D plane. Moreover, computer 212 may provide, via network 510, the modified image information to electronic device 210. This modified image information may be received by electronic device 210 and may be presented to the user of electronic device 210 on the display.

Subsequently, the user may provide the annotation information specifying the annotation markers in the 2D plane to electronic device 210, which may communicate, via network 510, the annotation information to computer 212. Additionally, the user may provide the command or an instruction indicating that the annotation is complete to electronic device 210.

In response, electronic device 210 may provide, via network 510, the command to computer 212. Then, computer 212 may modify the image information to translate and rotate the 3D image back to the initial position and orientation. This revised image information may be provided by computer 212, via network 510, to electronic device 210, which may be presented to the user of electronic device 210 on the display as the 3D image.

Note that information in system 500 may be stored at one or more locations in system 500 (i.e., locally or remotely). Moreover, because this data may be sensitive in nature, it may be encrypted. For example, stored data and/or data communicated via network 510 may be encrypted.

FIG. 6 presents a block diagram illustrating a computer system 600 that performs methods 100 (FIGS. 1 and 2). Computer system 600 includes one or more processing units or processors 610, a communication interface 612, a user interface 614, and one or more signal lines 622 coupling these components together. Note that the one or more processors 610 may support parallel processing and/or multi-threaded operation, the communication interface 612 may have a persistent communication connection, and the one or more signal lines 622 may constitute a communication bus. Moreover, the user interface 614 may include: a display 616, a keyboard 618, and/or a pointer 620, such as a mouse.

Memory 624 in computer system 600 may include volatile memory and/or non-volatile memory. More specifically, memory 624 may include: ROM, RAM, EPROM, EEPROM, flash memory, one or more smart cards, one or more magnetic disc storage devices, and/or one or more optical storage devices. Memory 624 may store an operating system 626 that includes procedures (or a set of instructions) for handling various basic system services for performing hardware-dependent tasks. Memory 624 may also store procedures (or a set of instructions) in a communication module 628. These communication procedures may be used for communicating with one or more computers and/or servers, including computers and/or servers that are remotely located with respect to computer system 600.

Memory 624 may also include multiple program modules (or sets of instructions), including: imaging module 630 (or a set of instructions), analysis module 632 (or a set of instructions), and/or encryption module 634 (or a set of instructions). Note that one or more of these program modules (or sets of instructions) may constitute a computer-program mechanism.

During the analysis technique, imaging module 630 may receive from a user of electronic device 210 (FIGS. 2 and 4), via communication interface 612 and communication module 628, an instruction 636 (or a command) to provide one or more images 640 in data structure 638. (Alternatively, the one or more images 640 may be provided via communication interface 612 and communication module 628.) As shown in FIG. 7, which presents a block diagram illustrating data structure 638 that includes image data, entries in data structure 638 for the one or more images 640 may include: features 712 (or anatomical structures), annotation markers 652 associated with features 712, geometric information 654 associated with features 652 (such as a size of one of features 652), and/or spatial information 656 (such as a position and/or orientation of one of features 652). While not shown in FIG. 7, the image data may include: image-parallax information, motion-parallax information and/or prehension information.

Referring back to FIG. 6, in response to instruction 636, imaging module 630 may access the one or more images 640 in data structure 638. Then, imaging module 630 may generate and may provide, via communication module 628 and communication interface 612, image information 642 specifying the 3D image of the portion of the individual based on the one or more images 640.

Then, analysis module 632 may receive, via communication interface 612 and communication module 628, plane information 644 specifying the 2D plane in the 3D image. In response, analysis module 632 may determine modified image information 646 by translating and rotating the 3D image so that the 2D plane is presented on a reference 2D plane 648 of a display (on which the 3D image is presented) with the orientation parallel to the reference 2D plane. Moreover, analysis module 632 may provide, via communication module 628 and communication interface 612, modified image information 646.

Subsequently, analysis module 632 may receive, via communication interface 612 and communication module 628, annotation information 650 specifying annotation markers 652 in the 2D plane. Analysis module 632 may calculate geometric information 654 and/or spatial information 656 based on annotation markers 652.

Furthermore, imaging module 630 may receive, via communication interface 612 and communication module 628, command 658 that the annotation of one or more of features 712 (FIG. 7) is complete. In response, imaging module 630 may provide, via communication module 628 and communication interface 612, image information 642. Alternatively, imaging module 632 may modify modified image information 646 to translate and rotate the 3D image back to the initial position and orientation (i.e., imaging module 632 may generate image information 642), and then imaging module 632 may provide, via communication module 628 and communication interface 612, image information 642.

Because information used in the analysis technique may be sensitive in nature, in some embodiments at least some of the data stored in memory 624 and/or at least some of the data communicated using communication module 628 is encrypted or decrypted using encryption module 634.

Instructions in the various modules in memory 624 may be implemented in: a high-level procedural language, an object-oriented programming language, and/or in an assembly or machine language. Note that the programming language may be compiled or interpreted, e.g., configurable or configured, to be executed by the one or more processors 610.

Although computer system 600 is illustrated as having a number of discrete items, FIG. 6 is intended to be a functional description of the various features that may be present in computer system 600 rather than a structural schematic of the embodiments described herein. In some embodiments, some or all of the functionality of computer system 600 may be implemented in one or more application-specific integrated circuits (ASICs) and/or one or more digital signal processors (DSPs).

Computer system 600, as well as electronic devices, computers and servers in system 600, may include one of a variety of devices capable of manipulating computer-readable data or communicating such data between two or more computing systems over a network, including: a personal computer, a laptop computer, a tablet computer, a mainframe computer, a portable electronic device (such as a cellular telephone or PDA), a server, and/or a client computer (in a client-server architecture). Moreover, network 510 (FIG. 5) may include: the Internet, World Wide Web (WWW), an intranet, a cellular-telephone network, LAN, WAN, MAN, or a combination of networks, or other technology enabling communication between computing systems.

Electronic device 210 (FIGS. 2 and 4), computer 212 (FIGS. 2 and 4), system 500 (FIG. 5), computer system 600 and/or data structure 638 (FIGS. 6 and 7) may include fewer components or additional components. Moreover, two or more components may be combined into a single component, and/or a position of one or more components may be changed. In some embodiments, the functionality of electronic device 210 (FIGS. 2 and 4), computer 212 (FIGS. 2 and 4), system 500 (FIG. 5), computer system 600 and/or data structure 638 (FIGS. 6 and 7) may be implemented more in hardware and less in software, or less in hardware and more in software, as is known in the art.

While the preceding embodiments illustrated the use of the analysis technique with medical images, in other embodiments the analysis technique is used with images in other types of applications, including non-medical applications. Consequently, in these other embodiments, the 3D image may be of an object other than an individual or an animal, including inanimate objects, materials, products, etc.

In the preceding description, we refer to 'some embodiments.' Note that 'some embodiments' describes a subset of all of the possible embodiments, but does not always specify the same subset of embodiments.

The foregoing description is intended to enable any person skilled in the art to make and use the disclosure, and is provided in the context of a particular application and its requirements. Moreover, the foregoing descriptions of embodiments of the present disclosure have been presented for purposes of illustration and description only. They are not intended to be exhaustive or to limit the present disclosure to the forms disclosed. Accordingly, many modifications and variations will be apparent to practitioners skilled in the art, and the general principles defined herein may be applied to other embodiments and applications without departing from the spirit and scope of the present disclosure. Additionally, the discussion of the preceding embodiments is not intended to limit the present disclosure. Thus, the present disclosure is not intended to be limited to the embodiments shown, but is to be accorded the widest scope consistent with the principles and features disclosed herein.

What is claimed is:

1. A computer-implemented method for facilitating detailed annotation of an anatomical structure, the method comprising:
    providing, on a display, a three-dimensional (3D) image of a portion of an individual, wherein the 3D image has an initial position and orientation;
    receiving information specifying a two-dimensional (2D) plane in the 3D image, wherein the 2D plane has an arbitrary angular position relative to the initial orientation;
    using the computer, translating and rotating the 3D image so that the 2D plane is presented in a reference 2D plane of the display with an orientation parallel to an orientation of the reference 2D plane, wherein a normal of the reference 2D plane is perpendicular to a plane of the display, and wherein, prior to the translating and the rotating, the angular position is different than that of the reference 2D plane and is different from a predefined orientation of slices in the 3D image;
    receiving information specifying the detailed annotation in the 2D plane, wherein the detailed annotation includes at least one of: a size of the anatomical structure based on annotation markers, an orientation of the anatomical structure, a direction of the anatomical structure and a location of the anatomical structure; and
    after the annotation is complete, translating and rotating the 3D image back to the initial position and orientation.

2. The method of claim 1, wherein the 3D image includes a stereoscopic image.

3. The method of claim 1, wherein the information specifying the detailed annotation is received from an interaction tool.

4. The method of claim 1, wherein the information specifying the detailed annotation corresponds to haptic interaction between a digit of a user and the display.

5. The method of claim 1, wherein the method further comprises, prior to translating and rotating the 3D image back to the initial orientation, receiving a command indicating that the annotation is complete.

6. The method of claim 1, wherein the 2D plane is positioned at a zero parallax position so that 3D information in the 2D plane is perceived as 2D information.

7. The method of claim 1, wherein the angular position is at an oblique angle relative to a symmetry axis of the individual.

8. The method of claim 1, wherein the 3D image corresponds to one of: a cross section of a volume, and a multiplanar-reconstruction image.

9. A non-transitory computer-readable storage medium for use in conjunction with a computer system, the computer-readable storage medium storing a program module, wherein, when executed by the computer system, the program module causes the computer system to facilitate detailed annotation of an anatomical structure by performing one or more operations comprising:
    providing, on a display, a three-dimensional (3D) image of a portion of an individual, wherein the 3D image has an initial position and orientation;
    receiving information specifying a two-dimensional (2D) plane in the 3D image, wherein the 2D plane has an arbitrary angular position relative to the initial orientation; translating and rotating the 3D image so that the 2D plane is presented in a reference 2D plane of the display with an orientation parallel to an orientation of the reference 2D plane, wherein a normal of the reference 2D plane is perpendicular to a plane of the display, and wherein, prior to executing the translating and the rotating, the angular position is different than that of the reference 2D plane and is different from a predefined orientation of slices in the 3D image;
    receiving information specifying detailed annotation in the 2D plane, wherein the detailed annotation includes at least one of: a size of the anatomical structure based on annotation markers, an orientation of the anatomical structure, a direction of the anatomical structure and a location of the anatomical structure; and
    translating and rotating the 3D image back to the initial position and orientation after the annotation is complete.

10. The computer-readable storage medium of claim 9, wherein the 3D image includes a stereoscopic image.

11. The computer-readable storage medium of claim 9, wherein the information specifying the detailed annotation is received from an interaction tool.

12. The computer-readable storage medium of claim 9, wherein the information specifying the detailed annotation corresponds to haptic interaction between a digit of a user and the display.

13. The computer-readable storage medium of claim 9, wherein the one or more operations comprise, prior to rotating the 3D image back to the initial orientation, receiving a command indicating that the annotation is complete.

14. The computer-readable storage medium of claim 9, wherein the 2D plane is positioned at a zero parallax position so that 3D information in the 2D plane is perceived as 2D information.

15. The computer-readable storage medium of claim 9, wherein the angular position is at an oblique angle relative to a symmetry axis of the individual.

16. The computer-readable storage medium of claim 9, wherein the 3D image corresponds to one of: a cross section of a volume, and a multiplanar-reconstruction image.

17. A computer system, comprising:
    a processor;
    memory storing a program module, wherein, when executed by the processor, the program module causes the computer system to facilitate detailed annotation of an anatomical structure by performing one or more operations comprising:
        providing, on a display, a three-dimensional (3D) image of a portion of an individual, wherein the 3D image has an initial position and orientation;

receiving information specifying a two-dimensional (2D) plane in the 3D image, wherein the 2D plane has an arbitrary angular position relative to the initial orientation;

translating and rotating the 3D image so that the 2D plane is presented in a reference 2D plane of the display with an orientation parallel to an orientation of the reference 2D plane, wherein a normal of the reference 2D plane is perpendicular to a plane of the display, and wherein, prior to the translating and the rotating, the angular position is different than that of the reference 2D plane and is different from a predefined orientation of slices in the 3D image;

receiving information specifying detailed annotation in the 2D plane, wherein the detailed annotation includes at least one of: a size of the anatomical structure based on annotation markers, an orientation of the anatomical structure, a direction of the anatomical structure and a location of the anatomical structure; and translating and rotating the 3D image back to the initial position and orientation after the annotation is complete.

18. The computer system of claim 17, wherein the 2D plane is positioned at a zero parallax position so that 3D information in the 2D plane is perceived as 2D information.

19. The computer system of claim 17, wherein the angular position is at an oblique angle relative to a symmetry axis of the individual.

20. The computer system of claim 17, wherein the 3D image corresponds to one of: a cross section of a volume, and a multiplanar-reconstruction image.

* * * * *